(12) United States Patent
Guerreschi (10) Patent No.: US 10,595,988 B2
(45) Date of Patent: Mar. 24, 2020

(54) COSMETIC CORNEAL INLAY AND IMPLANTATION METHOD THEREOF

(71) Applicant: OPHTA INNOVATIONS INC., Quebec (CA)

(72) Inventor: Francesco Maria Guerreschi, Grosseto (IT)

(73) Assignee: OPHTA INNOVATIONS INC., Montreal (CA)

( * ) Notice: Subject to any disclaimer, the term of this patent is extended or adjusted under 35 U.S.C. 154(b) by 97 days.

(21) Appl. No.: 15/524,770

(22) PCT Filed: Nov. 5, 2015

(86) PCT No.: PCT/IB2015/058549
§ 371 (c)(1),
(2) Date: May 5, 2017

(87) PCT Pub. No.: WO2016/071861
PCT Pub. Date: May 12, 2016

(65) Prior Publication Data
US 2017/0319330 A1    Nov. 9, 2017

(30) Foreign Application Priority Data
Nov. 6, 2014   (IT) .......................... RM2014A000649

(51) Int. Cl.
*A61F 2/14*         (2006.01)
(52) U.S. Cl.
CPC ............ *A61F 2/1451* (2015.04); *A61F 2/147* (2013.01); *A61F 2/148* (2013.01); *A61F 2/15* (2015.04); *A61F 2/14* (2013.01)

(58) Field of Classification Search
CPC .......... A61F 2/1451; A61F 2/15; A61F 2/147; A61F 2/148; A61F 2/14
See application file for complete search history.

(56) References Cited

U.S. PATENT DOCUMENTS

| | | | |
|---|---|---|---|
| 7,722,669 | B2 | 5/2010 | Foulkes |
| 2007/0168025 | A1 | 7/2007 | Darougar et al. |
| 2012/0143325 | A1 | 6/2012 | Christie et al. |

(Continued)

FOREIGN PATENT DOCUMENTS

| | | |
|---|---|---|
| DE | 39 26 536 A1 | 2/1991 |
| EP | 1 402 851 A1 | 3/2004 |
| WO | 00/67677 A1 | 11/2000 |

OTHER PUBLICATIONS

International Search Report, dated May 17, 2016, from corresponding PCT application.

*Primary Examiner* — Christopher D. Prone
*Assistant Examiner* — Christine L Nelson
(74) *Attorney, Agent, or Firm* — Young & Thompson (57) ABSTRACT

Disclosed is an intrastromal insert, already preformed, of solid, transparent, impermeable, biocompatible, physiologically inert and chemically resistant material, with notches allowing the passage of metabolites, substances, cells or portions thereof, and drugs, configured to receive printing, which is adapted in the space of the corneal stroma to change the eye color and/or to solve the problem of insufficient pigmentation of the iris. The method and the related component to change, permanently and reversibly, the eye color for aesthetic purposes are described as well.

19 Claims, 7 Drawing Sheets

(56) References Cited

U.S. PATENT DOCUMENTS

2012/0245683 A1 9/2012 Christie et al.
2013/0123916 A1* 5/2013 Nigam .................... A61F 2/148
                                                        623/5.11

* cited by examiner

COSMETIC CORNEAL INLAY AND IMPLANTATION METHOD THEREOF

FIELD OF THE INVENTION

The present invention relates to the eye cosmetology and aesthetic and functional refractive surgery, more precisely it relates to an insert, made of a biocompatible material, waterproof, colored, cut and carved to change the color and appearance of the eye, improving the ability to absorb radiation, normalize the function of the iris, whenever anatomically compromised, and the method for insertion thereof within the cornea of the eye.

BACKGROUND

The iris is a membranous ocular structure, situated at the rear of the cornea and and in the front of the crystalline lens, it defines and surrounds the pupillary opening whose diameter can change thanks to the movements of the iris. It has the shape of a circular disc and diaphragm acts as a diaphragm allowing light to enter the inner part of the eye. The main function of the iris is adjusting the amount of light that strikes the retina, both to protect the retina and to improve vision since, as in conditions of strong brightness, the restriction of the pupil ensures increased depth of focus expressed in dioptries and reduction of aberrations.

The pupil contraction is achieved through the sphincter muscle of the pupil, which surrounds the the pupil hedge (miosis); while through the dilator muscle of the pupil, radially arranged, it takes the dilation thereof (mydriasis).

The iris is pigmented, varying in color. The most common colors range from dark brown to light brown, more frequent in the Southern Caucasians, Asians and Negroids; fairly widespread, especially among Caucasian populations, are dark green tending to brown shades; then there are shades of gray, blue, blue and green light, mostly frequent in Northern Caucasians.

The biological function of the iris is very important, in fact, excessive exposure to sunlight can contribute to the development of cataracts or macular degeneration. Subjects with insufficient pigmentation are more sensitive to glare and predisposed to some eye diseases.

The coloration of the iris depends on the amount of melanin present. A greater amount of pigment in the iris of the eye yields a darker coloration, greater level of protection from ultraviolet radiation, and lower sensitivity to bright light.

In addition to the specific task to control the quantity of light that penetrates in the eye, by adjusting the amplitude of the pupil based on the brightness of the surrounding environment, to the iris is universally recognized an aesthetic function.

Thanks to the evoluting technologies applied to the production of contact lenses, it is now possible to temporarily change the eye color by using contact lenses, suitably pigmented with colors and designs different from the below iris. The cosmetic contact lenses should be regularly removed and, however, they can still provide risks and problems such as infections of the anterior segment of the eye, inflammatory reactions to the bulbar and tarsal conjunctiva, intolerance to the materials they are constituted of, or to the liquid solution wherein they are maintained, resulting in alterations of the cornea and relative decrease of visual acuity. Contact lenses also can be worn by many individuals, including people with dry eye syndrome or chronic diseases of the corneal surface and the conjunctiva.

Refractive surgical techniques providing for the introduction of inserts in the corneal stroma in order to correct visual defects such as myopia, hyperopia and astigmatism, or corneal insert restricting the pupillary aperture in order to allow a better near vision, have shown good tolerability without drawbacks. Hence, also the modern eye cosmetology has adapted and proposed artificial iris implants, widely used in classic ophthalmics to control glare and photophobia caused by iris defects, congenital or post-traumatic, complete (aniridia) or partial (colobomas), as implants developed to change eye color.

The U.S. Pat. No. 7,722,669 relates to a method for changing eye color comprising forming a coplanar annular channel around the pupil in the corneal stroma, by means of laser or surgical techniques, extending from the pupillary hedge up toward the limbus. The method provides that a biocompatible material, at least partially opacified, is inserted into the channel. The biocompatible material according to the invention is a dispersion of particles comprising an opacified material, permeable to be injected, hence in the form of liquid or hydrogel. Alternatively, the biocompatible material may include a thin layer of polymeric material, as a slurry comprising an opacified material.

This mash gives a homogeneous and opaque color quite far from iris natural aesthetic iris.

Although the subject-matter described in U.S. Pat. No. 7,722,669 is a permanent or semi-permanent method, to change the color of the eye which provides several benefits over the corneal contact lenses method, however, it does not totally solve some problems related to the particular conformation of the annular channel wherein the biocompatible material is inserted to give the new color. The realization of a intrastromal channel to be filled with a gelatinous colored mass, implies the occurrence of tensions on the corneal structure that, above certain thickness, can vary the curvature in its central portion, or areas involved in vision. However, the method of such US patent does not provide a technique able of ensuring the uniformity of layer thickness, of the order of 3-5 microns. Such uniformity, if not maintained, can generate different forces causing the occurrence of irregular astigmatisms, which, although minor, definitely interfere with the quality of vision. A further disadvantage is that to restore the transparency of the cornea the gelatinous slurry has to be aspirated from the tunnel in which it was placed. Therefore, needle cannulae, connected to vacuum systems or irrigation—suction, more or less simple, which through various incisions have to enter the route of the tunnel, with the consequent invasiveness on the corneal tissues should be used.

The US patent application 2012/0143325 describes corneal inlays and methods of improving vision of a patient by using said corneal inlays. Said application is directed to corneal inlays designed as intrastromal corneal inserts constituted by a film of solid transparent, impermeable, biocompatible, physiologically inert, and chemically resistant material, designed to receive any type of print, configured to position an opening within optical path of the eye for compensating for for inadequate optical performance of the eye, such as presbyopia, increasing the depth of focus of the patient. The invention described in US 2012/0143325, as most optical devices designed for capsular bag implantation, is preferably constituted of polyvinylidene fluoride (PVDF). PVDF has desirable characteristics to be used in ocular inlays such as being relatively chemically inert and having a relatively high UV resistance. Furthermore, according to said invention, PVDF can be made opaque by opacification agents providing sufficient opacity to produce the sought depth of field improvements. According to US 2012/0143325 the insertion of the implant affect the pupillary region because it has to magnify the vision; the inlays extend from the inner periphery at a radial distance of 0.8 mm to the outer periphery at a radial distance of 1.9 mm. In general, the thickness of the inlay is within the range of from about 1 to about 40 micron, and often in the range from about 5 to about 20 micron. In preferred embodiments the thicknesses is about 5 or 10 micron. Of course, considering the aim of the ocular device and moreover the site of insertion, the selection of the thickness range values of any corneal inlay cannot deviate from that representation.

For applying the corneal inlay to the eye of a patient according to US 2012/0143325 various techniques may be employed to position the device at different depths or between different layers within the cornea. In particular a corneal flap of suitable depth is hinged open. The depth of the flap varies between about the outermost 20% and about the outermost 5% of the thickness of the cornea.

The US patent application 2012/0245683 describes a corneal implant adapted for implantation between layers of the cornea to focus an image on a retina of an eye including an inlay, an outer perimeter, and a clear central region capable of refracting light to compensate for a refractive error of an eye. The inlay also has an annular opaque region comprising a plurality of holes. The annular opaque region extends from the outer circumference of the inlay to the clear central portion. The opaque region extends over a minority of the surface area of the implant. According to the invention, the holes dispersed about the device in the non-transmissive region, have a double function, in fact, they have a configuration to provide an adequate amount of gripping or position holding capability. Once the ocular device is implanted in the stromal layer of the cornea, corneal tissue adjacent to the recesses swells or expands into the recesses. By permitting corneal tissue to expand into the recesses, the likelihood of the ocular device becoming displaced within the cornea after being implanted or to otherwise moving relative to the eye can be reduced. In some cases, the expansion of the corneal tissue into the recesses is due to osmotic pressure or an effect similar to a capillary effect. Furthermore, the holes preferably are also configured to maintain the transport of one or more nutrients across the device. Preferably, the holes provide sufficient flow of one or more nutrients across the device to prevent depletion of nutrients in the first corneal layer adjacent the anterior surface of the device. For example, in certain embodiments, the holes provide sufficient flow of glucose across the device between the corneal tissue layers adjacent the device to prevent glucose depletion that would harm the adjacent corneal tissue.

However, the technical solutions proposed by documents US 2012/0143325 and US 2012/0245683 aimed to compensate refractive error and loss of accommodation do not solve at all the technical problem of providing an corneal intrastromal insert configured to change the color and appearance of the eye, improving the ability to absorb radiation, normalizing the function of the iris, whenever anatomically compromised, and the method for insertion thereof within the cornea of the eye.

Therefore, it is strongly felt the need to have alternative methods to change the color of the eye, to normalize any structural abnormalities of the iris and to provide means of absorption of the electromagnetic radiation which do not present the disadvantages of the methods of the state of the art, while still ensuring the reversibility.

SUMMARY OF THE INVENTION

Therefore, object of the present invention is providing a method and the related means to change, permanently and reversibly, the eye color for aesthetic purposes.

Another object of the present invention is providing a method for changing the color of eyes, that also allows to normalize structural anomalies of the iris.

To this end the present invention provides the use of an intrastromal insert, already preformed, in solid and water-proof material, with notches allowing the passage of metabolites, substances, cells or portions thereof, and drugs, which is adapted in the space of the corneal stroma to change the eye color and/or to solve the problem of insufficient pigmentation of the iris.

It is a further object of the invention the method used to position said insert in the corneal stromal space, and the specifically designed tool used for positioning the insert.

Advantageously, this method makes use of the femtosecond laser technology, already successfully used with little risk of complications in the field of ophthalmology.

Object of the invention is finally a kit for the application of the insert comprising an insert pre-assembled on a device that makes possible the positioning of the insert in the annulus shape cutting created by femtosecond laser in the corneal stroma. The use of the kit is the prerogative of the medical staff that performs the insertion in surgical eye clinic.

Other objects, advantages and further features of the present invention will appear clearly from the detailed description of the invention, that with the accompanying drawings, describes preferred embodiments of the invention.

DETAILED DESCRIPTION OF THE INVENTION

Figure 1:
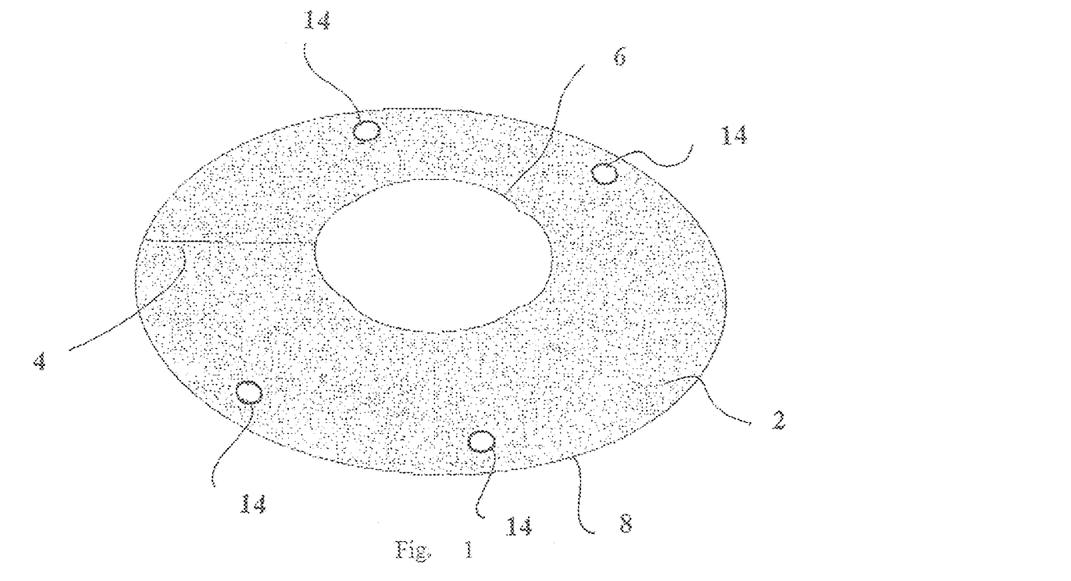
FIG. 1 shows the corneal insert according to a first embodiment.
Figure 2:
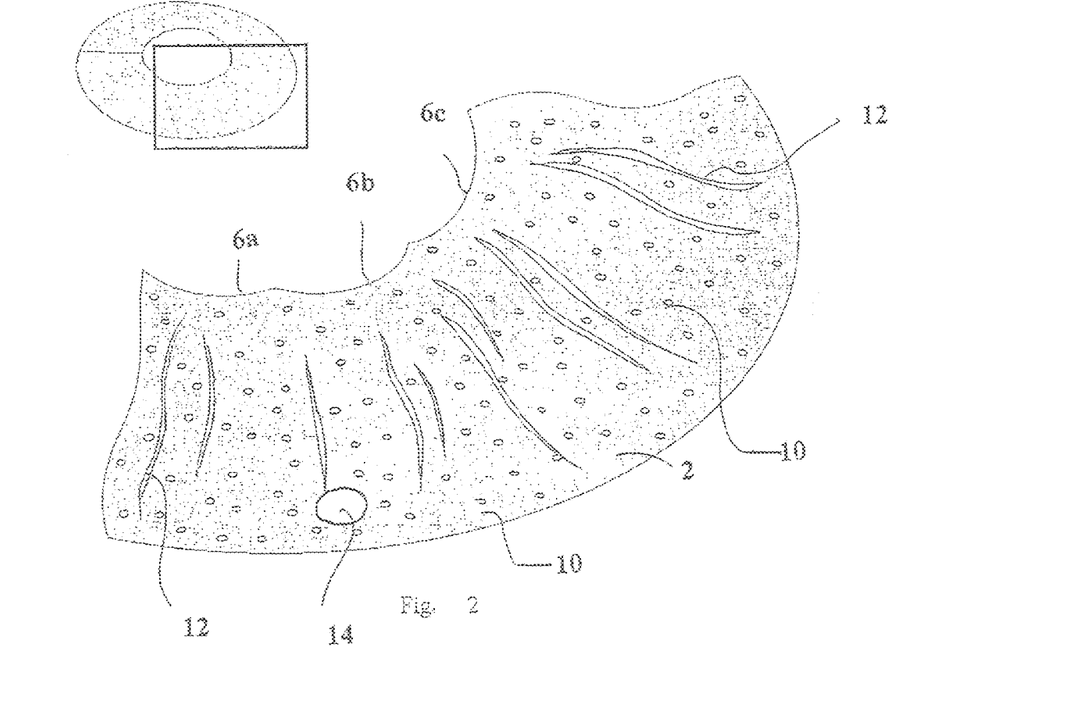
FIG. 2 shows a detailed portion of the corneal insert of FIG. 1, on a larger scale, which highlights its structure, with micro holes, notches and incisions.

With reference to FIGS. 1 and 2, the insert is obtained from a preformed film of polyvinylidene fluoride (PVDF), or of any physiologically inert film of material providing similar biocompatible, mechanical, thermal and electrical characteristics, combined with an excellent chemical resistance.

Polyvinylidene fluoride is already widely used in ophthalmic and in other medical fields exactly for its technical features. Furthermore, should be noted that the choice of the material used in ocular implants is quite limited. PVDF allows to produce a physiologically inert biocompatible film, up to the thickness compatible for ocular implants.

In particular, PVDF presents the following chemical-physical characteristics:

High maximum use temperature in air (150° C. continuous);
Good mechanical strength, creep resistance and stiffness;
Excellent chemical and hydrolysis resistance;
High impact resistance even at low temperatures;
Good ability of electrical insulation;
Good wear resistance and good sliding properties;
Good dimensional stability;
High resistance to UV rays;
Low intrinsic flammability;
Melting temperature at 175° C.;

The natural fluoropolyvinyldene color is white or transparent; it can be made of thin sheets having thickness in the order of microns, and can receive any type of printing.

In the ophthalmic industry fluoropolyvinyldene has already been used for the realization of corneal inserts for refractive purposes for the correction of presbyopia. It has already been implanted in hundreds of patients and in that specific use it has got the CE mark, while it is in the process of FDA approval.

According to the invention the film used to produce the insert has a thickness between 4.5 and 50 microns; this features guarantees the non-interference of the material with the corneal refractive ability. The realization of annulus shape insert, does not involve the exercise of any force on the central optical portion of cornea in front of pupil, left intact, therefore, with no effect changing the refractive properties of this latter portion of the cornea. In addition, the uniform thickness in all its portions of the manufactured constituting the insert, of, varies between 4.5 microns and 50 microns. Such thickness allows the rapprochement of the outer margin of the annulus with the outer portion of the cornea left intact by the procedure.

According to the invention the film can receive many colors given by non-toxic pigments deposition that reproduce the color pattern of the iris in the widest range of possible colors and fashions, from the most similar to the natural irises to more imaginative from the aesthetic point of view. Such color pattern is obtained by inkjet technology using non-toxic, water-repellent, UV-resistant inks in the order of picoliters.

As can be seen in FIG. 1, the PDVD film sheet, according to a preferred embodiment of the invention, is cut in order to obtain an annulus 2, pigmented, which, at any point of its outer perimeter 8, presents a cut 4, extending in a radial direction, across the width of the annulus, to the inner perimeter 6. The dimensions of the annulus 2 are variable depending on the size of the cornea to be treated and the pupillometry detected in the subject in mesopic conditions. The inner radius can vary between 1.75 mm and 2.50 mm, with discrete variations of 0.25 mm. The overall outer radius which may vary between 5 mm and 5.75 mm, with discrete variations of 0.25 mm.

According to a peculiar feature of the invention, as shown in FIG. 2, the profile of the central bore, or inner perimeter 6 of the annulus 2 is a multilobed line, wherein each lobe 6a, 6b, 6c and 6d, has the form of an arc of a circumference and wherein the lobes are two by two, symmetric and opposing. Such conformation, together with the radial cut 4 of the annulus 2, facilitates the adaptation of the surface of the insert to the surface of the corneal cap realized by the laser technology. In fact, the arc of circumference, allows to distribute the forces that may originate during the operation of insertion constituting an anti-tear system.

The invention allows to provide corneal implants in several models with different color and printing pattern.

Approaching the two free ends resulting from the radial cut 4, the annulus 2 assumes a three-dimensional structure so as to have a curvature adapted to that of the cornea and thus marrying the corneal surface.

This particular shape also allows the positioning of the insert below the corneal cap created by laser technique, such as to circumvent, bilaterally, the central portion of the cornea left intact, as will be described below.

As illustrated in FIGS. 1 and 2, the annulus shaped insert (2), presents microholes (10), notches (12) and engravings or discontinuities allowing flat surface of the insert to adapt to the curved surface of the corneal cap realized with the laser in the corneal stroma without forming folds. Furthermore, the annulus (2) has four holes (14) that, having as reference the position of the cut 4 at 12 o'clock position, are respectively positioned at hours 2, 4, 8 and 10. The presence of micro-holes (10) and the notches (12), allows the passage of substances, gases, cells, or portions thereof, between the two portions of the corneal stroma separated from the insert itself.

Figure 3:
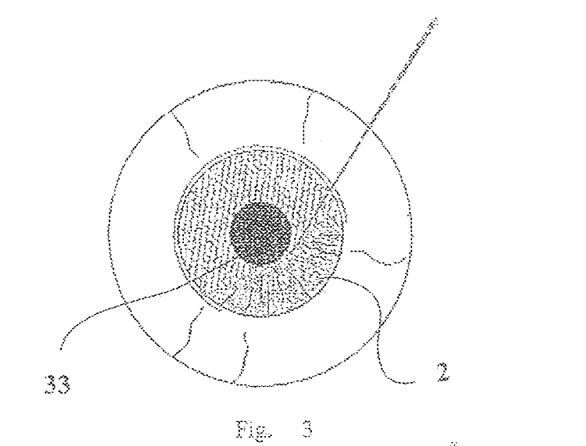
FIG. 3 shows, overhead view, the laser irradiation area (dotted) of the cornea of the eye.
Figure 4:
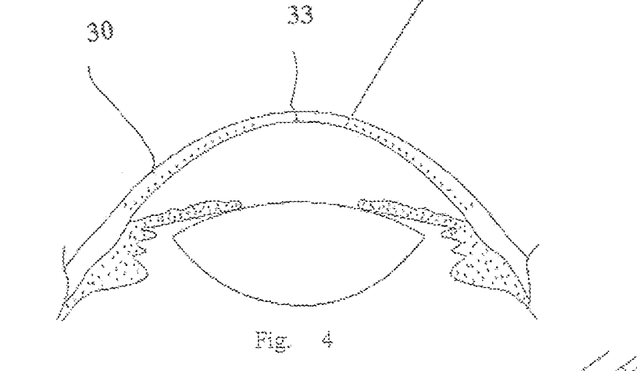
FIG. 4 shows, in cross section, the same pattern of laser irradiation of the cornea of the eye of FIG. 3.
Figure 5:
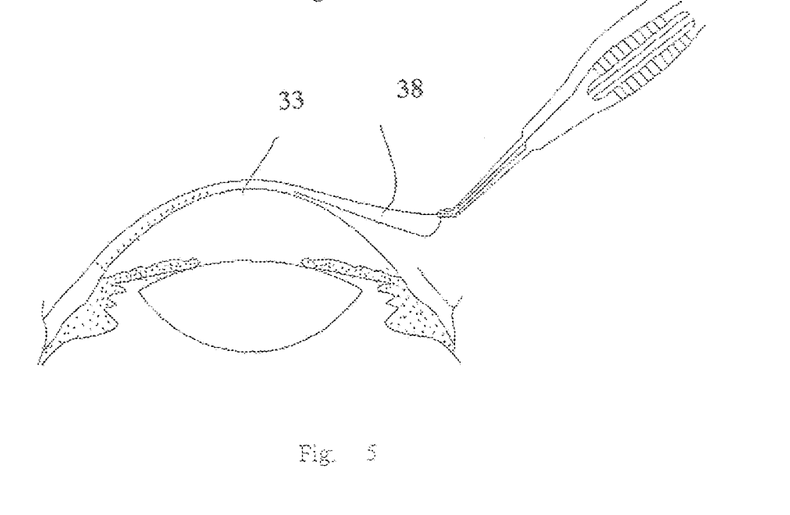
FIG. 5 shows the cross section of the eye with the flap of the corneal cap raised as a result of the cutting performed by femtolaser irradiation.

According to the invention, the insert of biocompatible material, waterproof, suitably colored, carved and cut, is inserted underneath the flaps of corneal tissue created by the cutting suitably realized through the laser technique as shown in FIGS. 3, 4 and 5. The carving pattern contributes to confer aesthetic design reproducing the natural pattern of the iris characterized by numerous crypts, additionally variants of human irises can be reproduced on the insert according to the invention by the above described printing technique.

The corneal flap (38) according to the invention is formed by separation in the corneal tissue produced by the femtosecond laser technique. The femtosecond laser technique, also known as femtolaser, is able to separate the corneal stroma. The name of the technique derives from the time taken by the laser to create the spots on the cornea: one millionth of a billionth of a second to produce the incisions useful to create the corneal cutting and hence the flap through which the insert is positioned.

The cutting leaves intact a wide circular area of corneal tissue at the pupillary foramen with a variable radius between 1.75 and 2.25 mm from the center of the cornea (FIG. 3) extending to the corneal limbus where the cutting becomes more superficial. The cutting produced in the corneal stroma wherein the annulus insert will be positioned has an annulus shape as well. The cutting extends over the entire circumference of the cornea and presents a zone of continuity in the central corneal portion (33), left intact by the laser treatment (FIG. 4). Therefore, it is evident that the present invention differs from the prior art solutions, namely that of patent application US 2012/0245683 and US 2012/0143325, wherein the corneal inlays are configured to form a central opening, within the optical path of the eye, to compensate for inadequate optical performance of the eye. Such central aperture of the corneal inlay can have many different shapes (hexagon, octagon, oval star, etc . . . ) and many positions (centered, off-centered, etc . . . ) to provide different effect to improve the patient's vision. Adversely, in the present ocular device the optical path is not affected, in accordance with the aim of the invention addressed to change the aesthetic aspect of the iris.

According to the invention, in the corneal stroma a sort of pocket with free outer margin, carried out between 100 and 200 microns from the outer border, or from the inner border, or in the portions of the stroma less rich in keratocytes, so as to minimize the cellular irritating processes responsible for a possible blurring (FIG. 5). The cutting creates a kind of corneal cap with free margins at the external perimeter and continuous with the corneal stroma in the central part thereof.

The achievement of the annulus cutting by means of femtosecond laser is computer assisted with a specifically dedicated software, that is not within the scope of the invention.

In particular, the technical features of the insert thickness variable between 4.5 and 50 microns, and of the way to produce the annulus cutting are such as to give no effects on the ability of the refractive corneal portion left intact at the pupillary foramen.

Another typical feature characteristic of the method according to the invention consists in the specific positioning mode of the insert in the corneal stroma underneath the flaps of the cutting. This procedure is assisted by the use of a specific tool (21), or device, allowing the positioning of the insert in the pocket created by femtosecond laser technology in the corneal stroma.

Figures 6, 6A, 6B, 6C:
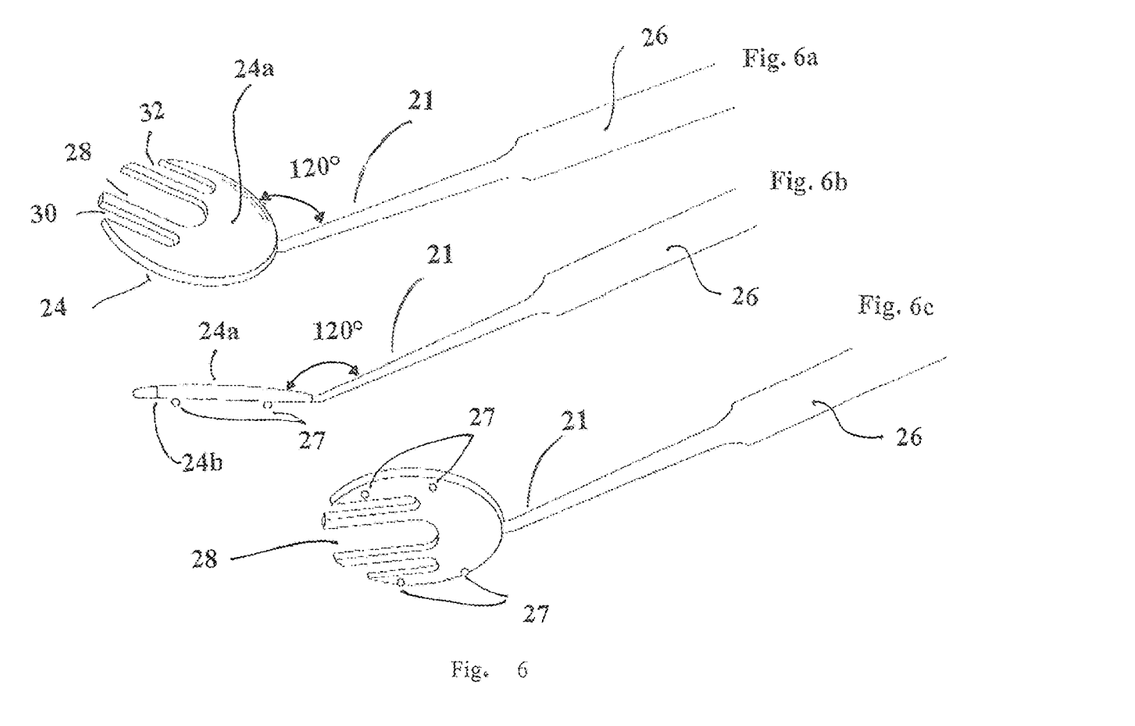
FIGS. 6a, 6b and 6c in perspective views respectively from above, laterally and from below, the insert holder used to position the insert in the corneal stroma, below the annulus cutting in the corneal tissue created by the femtolaser technique of FIG. 5.
Figure 7:
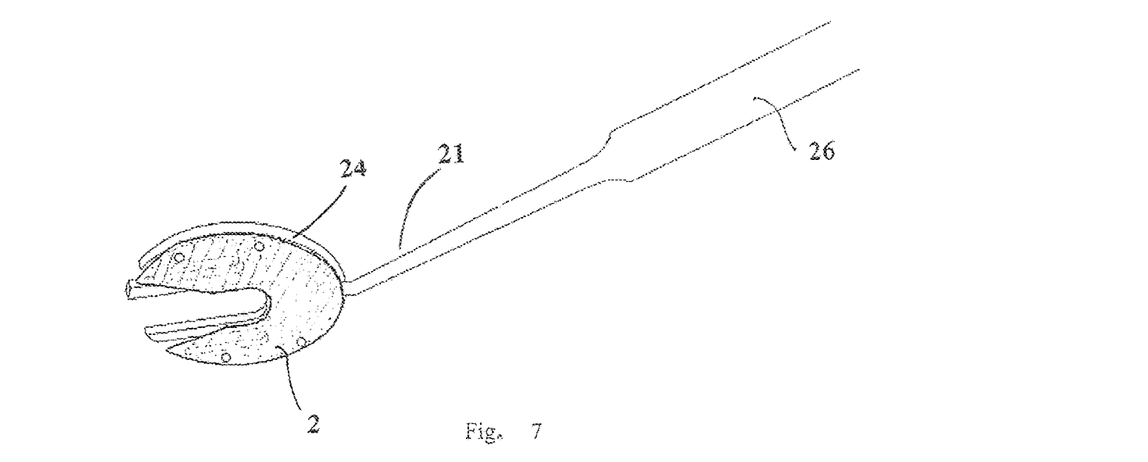
FIG. 7 shows in perspective view from below the insert-holder allowing to load the insert in the conformation with open cutting ends.
Figures 8, 9:
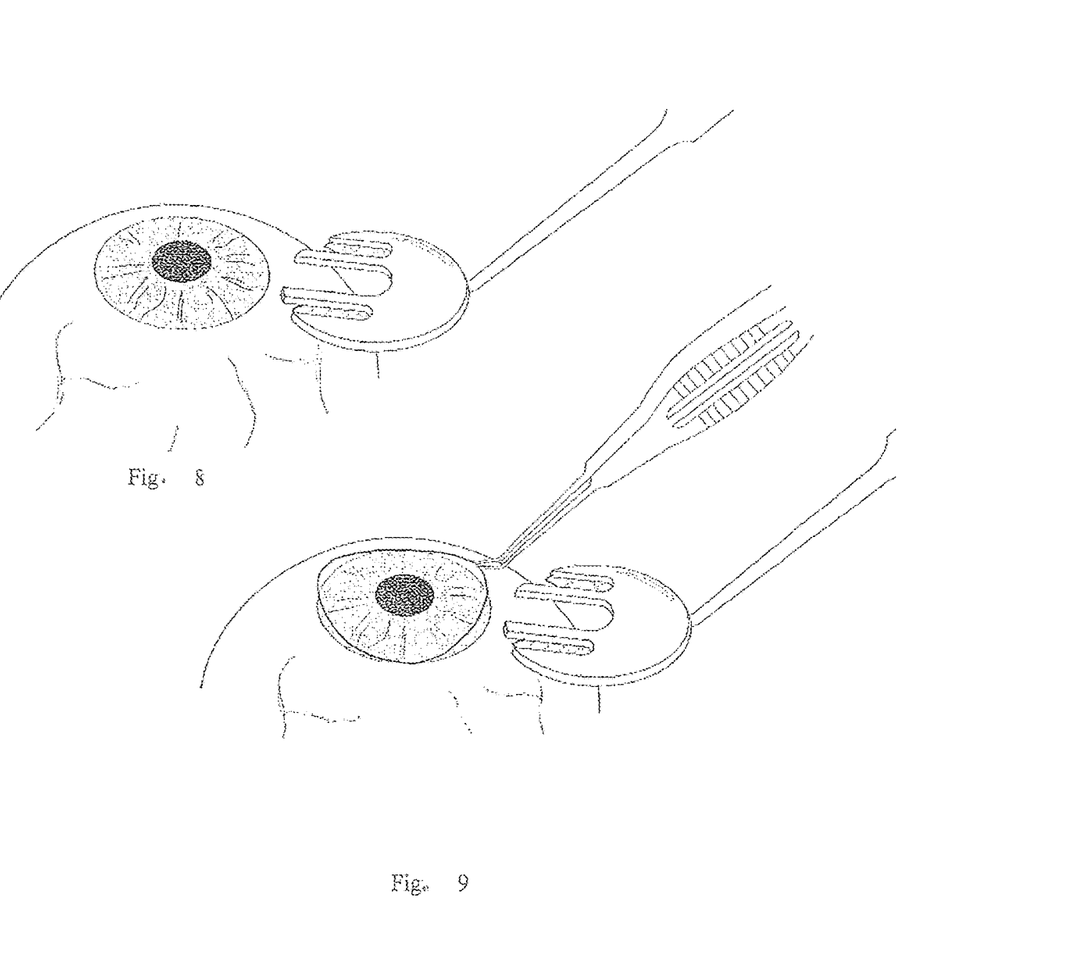
FIGS. 8 and 9 show the approaching step of the insert holder to the eye and the use of a thin claws tweezers to lift the corneal cutting flap.

Such a device, or insert holder (21), as shown in FIGS. 6a, 6b and 6c, has the form of a slotted plate (24) with a handle (26). The plate (24) of the device (21) for the application of the insert (2) has variable size in accordance with the various models and sizes of the insert to be applied, as described above, with radius increased by 0.5 mm radius. The handle (26) of the device, with non-slip finishing, has a length between 8 and 16 cm. The upper surface of the plate (24a) and the axis of the handle (26) form an angle variable between 120 and 160 degrees. The upper and lower faces of the plate are smooth, the upper surface (24a) is convex, while the lower surface (24b) is concave. In its lower face (24b) the plate is provided with four pins (27) wherein the coloured corneal insert can be engaged through the four holes (14) as described above.

In a preferred embodiment, (FIGS. 6a, 6b and 6c), the plate has three slots with the same orientation, a central one (28) 5 mm width of and two side slots (30 and 32), both 1.5 mm width.

Figures 10, 11:
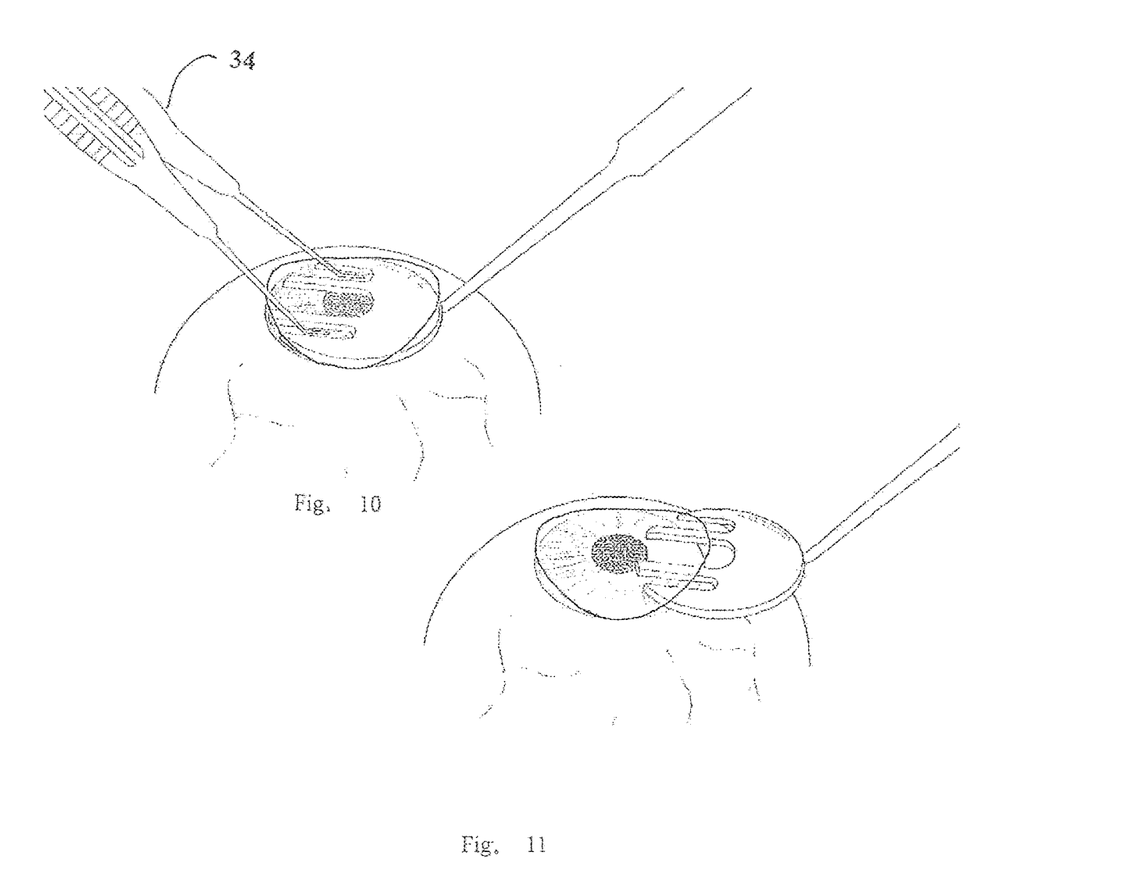
FIG. 10 shows the positioning step of the insert with open cutting ends open underneath the corneal cutting flap by the insert holder and the fixing thereof in the thin claws tweezers of FIG. 9, inserted into the two slots formed in the plate of the insert holder.
FIG. 11 shows the insert holder while is extracted from the corneal annulus cutting site after downloading and positioning the insert.

In FIGS. 10 and 11 is illustrated the procedure for inserting the inlay (2). The central slot (28) of the insert holder (24) allows the insertion of the corneal insert, or inlay, under the corneal flap with the two free ends of the annulus (insert) (2) surrounding the area of continuity of the central cornea in correspondence of the pupil. The two side slots (30 and 32) serve to facilitate the detachment of the insert (2) from the plate (24a) when the insert (2), and the two ends thereof, are in their final position underneath the corneal cap (FIG. 10).

Figures 12A, 12B:
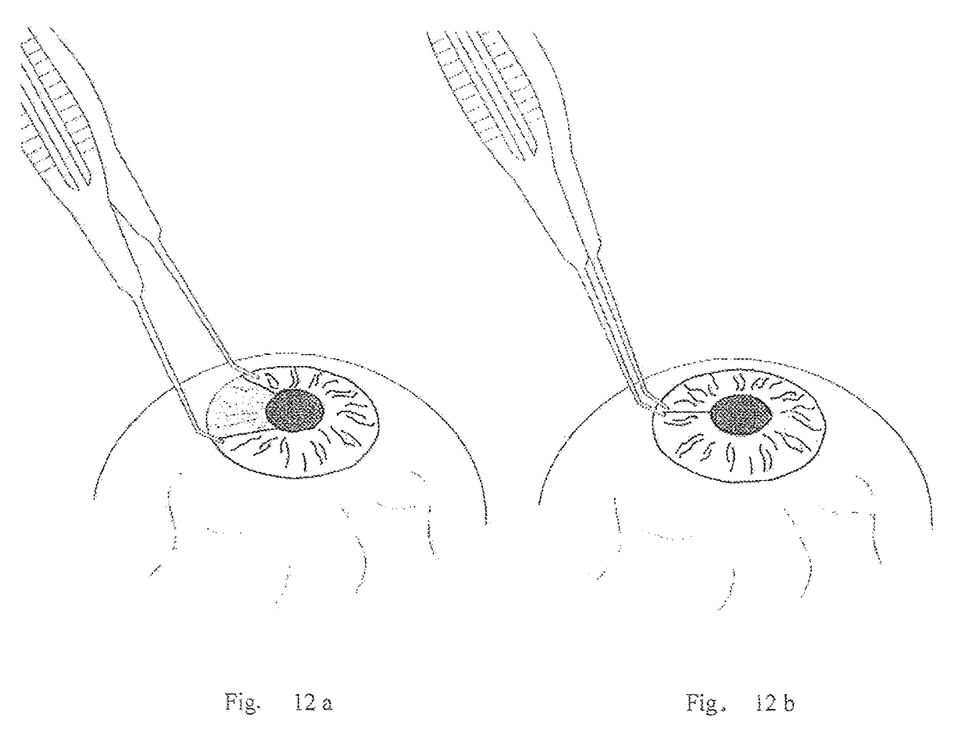
FIGS. 12a and 12b show the step wherein the free ends of the insert are arranged around the foramen pupillary are brought closer each other by means of the tweezers of FIG. 9.

The detachment of the insert (2) from the plate (24a) is facilitated through the use of thin tip tweezers 34, bent, non-traumatic, whose tips can be inserted into the two side slots of the plate carrying the insert (FIG. 11). The tweezers allows to manipulate the insert (2) in the pocket for the correct positioning of the same in the stroma up the juxtaposing the two free ends of the annulus (FIG. 12b).

Figure 13:
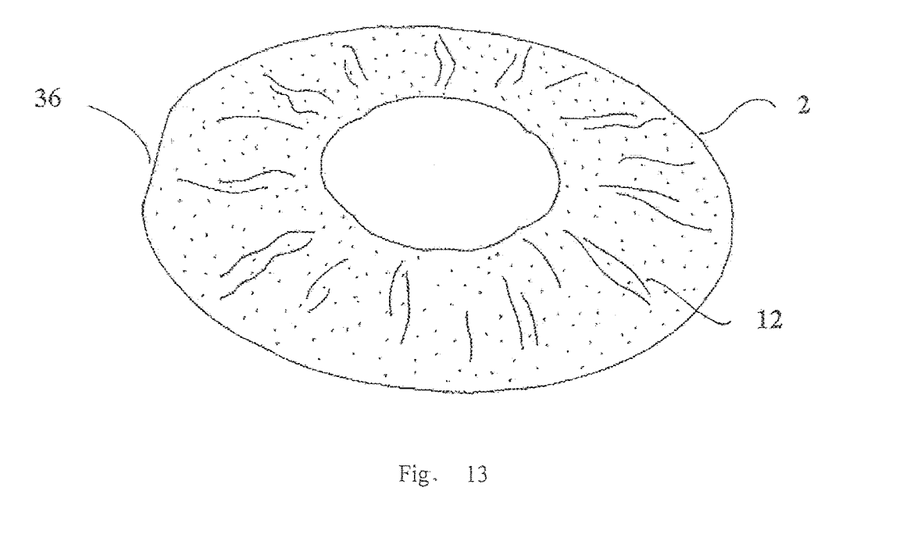
FIG. 13 shows in perspective view a variant of the insert without radial cut and with a rectilinear portion of the outer perimeter configured to be applied during LASIK refractive surgery.
Figure 14:
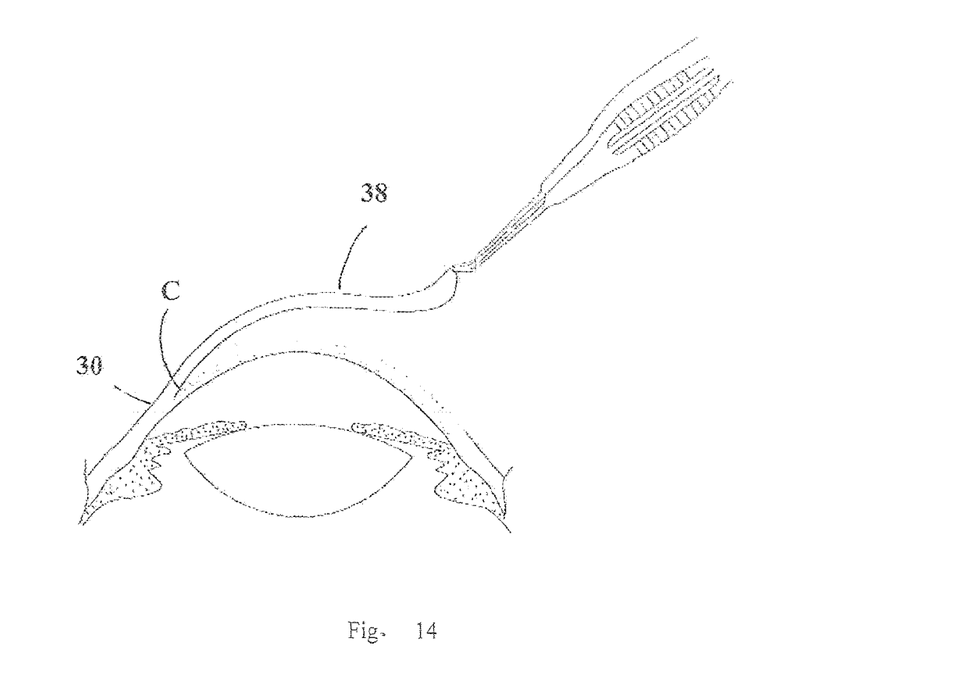
FIG. 14 shows the cross section of the eye with the flap of the corneal cap raised, ready for the insertion of the insert of FIG. 13, with the lateral portion of the cornea left intact by the standard LASIK procedure.

In another embodiment of the invention illustrated in FIGS. 13 and 14 the insert of biocompatible material, waterproof, suitably colored, carved and cut has an annulus shape, as described, with no radial cut. According to this latter embodiment the inlay of the invention can be applied during LASIK refractive surgery. In this embodiment, the insert presents a minus of material (36) forming in the annulus a circular segment such as to leave, perpendicularly to the circular segment, a 2.25 mm residual radial width. The annulus so configured is mm is suitable to be applied with the circular segment in correspondence of the portion of the cornea left intact by the standards LASIK procedure.

The method for changing the color of the eye for aesthetic purposes, according to the invention, allows to obtain a permanent result, but also provides the ability to restore in the subject the original situation, or to further change color, performing a simple procedure described below.

The method can be performed in an outpatient surgical eye clinic procedure and/or in day hospital; it is not particularly invasive, it does not present undue risk of side effects and it is not harmful for the eye health and the vision.

However, as it is a surgical intervention, a careful preliminary analysis phase of the subject is required, and a thorough checkup of the eye in order to measure and determine the eye pressure and a careful study of the conditions of the retina is mandatory.

In the light of the description provided the method allowing to change the eye color in a permanent and reversible manner according to the invention comprises:

1) irradiation of the cornea with the femtosecond laser (FIGS. 2 and 3);
2) preparation of the insert pre-loaded on the plate of the insert holder;
3) lifting the edges of the corneal flap;
4) positioning of the insert in the corneal stroma;
5) detachment of the insert from the plate of the insert holder;
6) handling of the insert to facilitate the proper positioning of the insert to marry the surface of the corneal stroma;
7) juxtaposition of the free ends of the corneal insert;
8) juxtaposition of corneal flaps to marry the top surface of the insert.

Both the implant and explants intervention are made under local anesthesia with instillation of anesthetic eye drops.

Due to the characteristics of the insert, of the insertion procedure itself, and of the application kit thereof the insertion technique is relatively simple and the procedure is easily tolerable to the subject that has to receive the insert. The choice of a solid material, also waterproof, makes easier the reversibility of the procedure allowing the patient to return to its original iris color or to further change it by the insertion of another insert. In particular, with regard to the reversibility of the procedure it is evident the advantage deriving from the use of a solid insert such as in the case of the invention compared to methods of the state of the art. In fact, in the case of use of pigmented hydrogel, as described in U.S. Pat. No. 7,722,669, to restore the state of transparency of the cornea there is the need to aspirate the layer of pigmented gelatinous mass from the tunnel wherein it was placed. This involves the use of needle-cannulas, connected to vacuum or irrigation-aspiration systems, which through various incisions have to enter the route of the tunnel with the consequent invasiveness on the corneal tissues. By using a solid insert according to the present invention, instead, it is sufficient to find the cleavage plane of the outer edge of the corneal cap, by a surgical spatula and remove the insert with tweezers, with no stress for the tissues, and even with the possibility to replace the insert with another one with different chromatic features. Therefore, the advantage concerning the reversibility of the insert and of the method according to the invention is quite evident.

The invention also provides a kit for the application of the insert comprising the described corneal insert of the appropriate size based on the size of the pupil of the subject, determined by the physician performing the implantation, with the chromatic pattern selected in a wide range of options such as to meet the aesthetic taste of the subject.

Each insert is pre-assembled on the insert holder according to the invention, as described above, that makes possible the positioning of the insert in the corneal pocket. Optionally, the kit also includes a tweezer to the correct and final positioning of the insert in the final seat in the corneal stroma. All elements of the kit are sterilized according to normal procedures known to the experts of the field.

The invention claimed is:

1. An intrastromal corneal insert constituted by a film of solid, transparent, impermeable, biocompatible, physiologically inert and chemically resistant material, having thickness between 4.5 and 50 μm, wherein the intrastromal corneal insert has a shape of an annulus of variable dimensions as a function of dimensions of a cornea in a subject who has to receive the insert and of pupillometry detected in mesopic conditions in the subject, wherein a central hole of the annulus has an inner perimeter in a form of a multilobed line, wherein each lobe has a shape of an arc of circumference and the lobes are two by two symmetric and opposing, and the annulus having four holes respectively positioned at 2, 4, 8, and 10 o'clock, wherein the insert has a plurality of chromatic patterns printed thereon, and wherein the patterns reproduce a chromatic pattern of an iris in the subject who has to receive the insert or of another chromatic pattern.

2. The intrastromal corneal insert according to claim 1, wherein an inner radius of the annulus ranges between 1.75 mm and 2.50 mm in discrete increments of 0.25 mm, and a total outer radius ranges between 5 mm and 5.75 mm with a value of 5.0 mm, 5.25 mm, 5.50 mm, or 5.75 mm.

3. The intrastromal corneal insert according to claim 2, wherein the annulus has microholes, notches, or incisions.

4. The intrastromal corneal insert according to claim 2, wherein the annulus has at any point of an outer perimeter (8) a cut extending in a radial direction across a width of the annulus itself to the inner perimeter.

5. The intrastromal corneal insert according to claim 2, having in the annulus a minus of material corresponding to a circular segment such as to leave, perpendicularly to the circular segment, a residual radial width of the annulus of 2.25 mm, configured to be applied in a course of LASIK refractive surgery.

6. The intrastromal corneal insert according to claim 2, wherein the material is polyvinylidene fluoride.

7. The intrastromal corneal insert according to claim 1, wherein the annulus has microholes, notches, or incisions.

8. The intrastromal corneal insert according to claim 7, wherein the annulus has at any point of an outer perimeter a cut extending in a radial direction across a width of the annulus itself to the inner perimeter.

9. The intrastromal corneal insert according to claim 7, having in the annulus a minus of material corresponding to a circular segment such as to leave, perpendicularly to the circular segment, a residual radial width of the annulus of 2.25 mm, configured to be applied in a course of LASIK refractive surgery.

10. The intrastromal corneal insert according to claim 1, wherein the annulus has at any point of an outer perimeter (8) a cut extending in a radial direction across a width of the annulus itself to the inner perimeter.

11. The intrastromal corneal insert according to claim 1, having in an outer perimeter of the annulus an absence of material corresponding to a circular segment of the inner perimeter of the central hole of the annulus such as to leave, perpendicularly to the circular segment, a residual radial width of the annulus of 2.25 mm, configured to be applied in the course of LASIK refractive surgery.

12. The intrastromal corneal insert according to claim 1, wherein the material is polyvinylidene fluoride.

13. The intrastromal corneal insert according to claim 1, wherein the chromatic patterns printed thereon comprise UV-resistant, hydrophobic, and non-toxic pigments from non-toxic, water repellent, UV resistant inks.

14. An insert-holder device designed to hold the intrastromal corneal insert of claim 1 and to position said insert in a pocket created by femtosecond laser technology in a corneal stroma, wherein the insert-holder device has a shape of a slotted plate having slots of variable dimensions according to dimensions of said insert, wherein a radius of the slotted plate is increased by 0.5 mm as compared to a radius of said insert,
provided with a handle with antislip finish,
wherein the handle has a length between 8 and 16 cm, and between a top surface of the plate and an axis of the handle an angle is formed between 120° and 160°, said plate being provided in its bottom face (24b) with four pins designed to engage the corneal insert via the four holes positioned respectively at 2, 4, 8 and 10 o'clock.

15. The insert-holder device according to claim 14, wherein the plate has three slots with a same orientation, being a central one 5 mm wide and two lateral ones 1.5 mm wide.

16. A kit for application of an intrastromal corneal insert, the kit comprising:
a) an intrastromal corneal insert constituted by a film of solid, transparent, impermeable, biocompatible, physiologically inert and chemically resistant material, having thickness between 4.5 and 50 μm, having shape of an annulus of variable dimensions as a function of dimensions of a cornea a subject who has to receive the insert and of pupillometry detected in mesopic conditions in the subject, wherein a central hole of the annulus has an inner perimeter in a form of a multilobed line, wherein each lobe has a shape of an arc of circumference and the lobes are two by two symmetric and opposing, and the annulus having four holes respectively positioned at 2, 4, 8, and 10 o'clock, wherein the insert has a plurality of chromatic patterns printed thereon, and wherein the patterns reproduce a chromatic pattern of an iris in the subject who has to receive the insert or of another chromatic pattern, wherein the annulus has at any point of an outer perimeter a cut extending in a radial direction across a width of the annulus itself to the inner perimeter;
  b) an insert-holder device of claim 14; and
  c) a pair of tweezers.

17. The kit for the application of the intrastromal corneal insert according to claim 16, wherein the insert is premounted on the insert-holder device.

18. A kit for application of an intrastromal corneal insert, comprising:
  a) an intrastromal corneal insert constituted by a film of solid, transparent, impermeable, biocompatible, physiologically inert and chemically resistant material, having thickness between 4.5 and 50 µm, having shape of an annulus of variable dimensions as a function of dimensions of a cornea and of a pupillometry detected in mesopic conditions in a subject who has to receive the insert, wherein a central hole of the annulus has an inner perimeter in a form of a multilobed line, wherein each lobe has a shape of an arc of circumference and the lobes are two by two symmetric and opposing, and the annulus having four holes respectively positioned at 2, 4, 8, and 10 o'clock, having a plurality of chromatic patterns thereon reproducing a chromatic pattern of an iris or of another chromatic pattern wherein a shape of an outer perimeter (8) of the annulus has an absence of material corresponding to a circular segment of the inner perimeter of the central hole of the annulus such as to leave, perpendicularly to the circular segment, a residual radial width of the annulus of 2.25 mm;
  b) an insert-holder device of claim 14; and
  c) a pair of tweezers.

19. A method for modifying the color of eyes in a permanent and reversible manner comprising the steps of:
  1) irradiation of a cornea of the eyes with femtosecond laser;
  2) loading the intrastromal corneal insert of claim 1 on an insert-holder device designed to hold the intrastromal corneal insert and to position said insert in a pocket created by femtosecond laser technology in a corneal stroma of the cornea, wherein the insert-holder device has a shape of a slotted plate having slots of variable dimensions according to dimensions of said insert, wherein a radius of the slotted plate is increased by 0.5 mm as compared to a radius of said insert, provided with a handle with antislip finish;
  3) lifting edges of a cap corneal of the cornea;
  4) positioning of said intrastromal corneal insert in the pocket created in the corneal stroma;
  5) detachment of said intrastromal corneal insert from the plate of the said insert-holder device;
  6) handling of said insert to facilitate a proper positioning of the insert to match a surface of the corneal stroma;
  7) juxtaposition of free ends of said corneal insert;
  8) juxtaposition of corneal flaps of the corneal cap to match a top surface of the intrastromal corneal insert.

\* \* \* \* \*